United States Patent
Isobe (10) Patent No.: US 12,036,579 B2
(45) Date of Patent: Jul. 16, 2024

(54) ULTRASOUND ENDOSCOPE AND INSERTION TUBE

(71) Applicant: OLYMPUS CORPORATION, Tokyo (JP)

(72) Inventor: Yosuke Isobe, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 408 days.

(21) Appl. No.: 17/400,652

(22) Filed: Aug. 12, 2021

(65) Prior Publication Data

US 2021/0369239 A1   Dec. 2, 2021

Related U.S. Application Data (63) Continuation of application No. PCT/JP2019/011531, filed on Mar. 19, 2019.

(51) Int. Cl.
*B06B 1/06* (2006.01)
*A61B 1/00* (2006.01)
(Continued)

(52) U.S. Cl.
CPC ........ *B06B 1/0633* (2013.01); *A61B 1/00071* (2013.01); *A61B 1/0008* (2013.01); (Continued)

(58) Field of Classification Search
CPC .............. A61B 1/00071; A61B 1/0008; A61B 1/00137; A61B 1/0011
See application file for complete search history.

(56) References Cited

U.S. PATENT DOCUMENTS 5,685,311 A * 11/1997 Hara .................... A61B 8/4488
                                                                 600/459
7,488,288 B2 * 2/2009 Tanaka ..................... A61B 8/12
                                                                 604/20
(Continued)

FOREIGN PATENT DOCUMENTS

JP    S62-177701 U    11/1987
JP       3619423 B2    2/2005
(Continued)

OTHER PUBLICATIONS

International Search Report dated Jun. 18, 2019 received in PCT/JP2019/011531.
English abstract only of JP 2001-314402 A.

*Primary Examiner* — Oommen Jacob
(74) *Attorney, Agent, or Firm* — Scully, Scott, Murphy & Presser, P.C.

(57) ABSTRACT

An ultrasound endoscope includes an insertion tube configured to be inserted into a subject, the insertion tube including a transducer that includes a plurality of piezoelectric devices that are aligned along a circumferential direction about a center axis of the insertion tube, an observation optical portion configured to capture a subject image, a first built-in material that is different from the observation optical portion, and a support configured to support the observation optical portion and the first built-in material, the transducer including a through hole configured to pierce through along the center axis to insert the support, and the support including a first groove that extends along the center axis, the first groove being configured to support the observation optical portion, and a second groove that extends along the center axis, the second groove being configured to support the first built-in material and communicate with the first groove.

22 Claims, 10 Drawing Sheets

(51) Int. Cl.
*A61B 1/015* (2006.01)
*A61B 1/018* (2006.01)
*A61B 8/00* (2006.01)
*A61B 8/12* (2006.01)

(52) U.S. Cl.
CPC .......... *A61B 1/00137* (2013.01); *A61B 1/015* (2013.01); *A61B 1/018* (2013.01); *A61B 8/12* (2013.01); *A61B 8/4494* (2013.01); *B06B 1/0607* (2013.01)

(56) References Cited

U.S. PATENT DOCUMENTS

| | | | | |
|---|---|---|---|---|
| 2001/0041839 A1* | 11/2001 | Ohara | ...................... | A61B 8/12 600/463 |
| 2001/0041841 A1 | 11/2001 | Ohara et al. | | |
| 2006/0025691 A1* | 2/2006 | Tanaka | ...................... | A61B 8/12 600/459 |
| 2007/0293762 A1* | 12/2007 | Sawada | ................. | B06B 1/0633 600/459 |
| 2008/0084137 A1* | 4/2008 | Wakabayashi | ......... | A61B 8/445 29/25.35 |
| 2008/0119738 A1* | 5/2008 | Imahashi | ........... | A61B 1/00114 600/182 |
| 2009/0204006 A1* | 8/2009 | Wakabayashi | ......... | A61B 8/445 600/463 |
| 2011/0230716 A1 | 9/2011 | Fujimoto | | |
| 2011/0275890 A1* | 11/2011 | Wang | .................... | A61B 8/4461 600/104 |
| 2013/0158410 A1* | 6/2013 | Ohgishi | ................. | A61B 1/005 600/462 |
| 2015/0265142 A1 | 9/2015 | Ogawa | | |
| 2021/0369239 A1* | 12/2021 | Isobe | ................. | A61B 1/00071 |

FOREIGN PATENT DOCUMENTS

| | | |
|---|---|---|
| JP | 2011-206416 A | 10/2011 |
| JP | 2013-248529 A | 12/2013 |
| WO | 2010/150666 A1 | 12/2010 |
| WO | 2014/208218 A1 | 12/2014 |

* cited by examiner

ULTRASOUND ENDOSCOPE AND INSERTION TUBE

CROSS-REFERENCE TO RELATED APPLICATION

This application is a continuation of International Application No. PCT/JP2019/011531, filed on Mar. 19, 2019, the entire contents of which are incorporated herein by reference.

BACKGROUND

1. Technical Field

The present disclosure relates to an ultrasound endoscope and an insertion tube.

2. Related Art

As an ultrasound endoscope having an insertion tube to be inserted into a subject, a direct radial ultrasound endoscope has been known (for example, Japanese Patent No. 3619423).

In the ultrasound endoscope described in Japanese Patent No. 3619423, an insertion tube includes a transducer including multiple piezoelectric devices that are aligned along a circumferential direction about a center axis of the insertion tube and that respectively emit ultrasound waves, an observation optical portion that captures an image of a subject, and a support that supports the observation optical portion.

In the transducer, a first through hole that pierces through along the center axis of the insertion tube is arranged. Moreover, in the support, a second through hole that pierces through along a center axis is arranged. The observation optical portion is supported by the support in a state of being inserted through the second through hole. Furthermore, the support is inserted in the first through hole while supporting the observation optical portion.

SUMMARY

In some embodiments, an ultrasound endoscope includes an insertion tube configured to be inserted into a subject, the insertion tube including a transducer that includes a plurality of piezoelectric devices that are aligned along a circumferential direction about a center axis of the insertion tube, each piezoelectric device being configured to emit ultrasound wave, an observation optical portion configured to capture a subject image, a first built-in material that is different from the observation optical portion, and a support configured to support the observation optical portion and the first built-in material, the transducer including a through hole configured to pierce through along the center axis to insert the support, and the support including a first groove that extends along the center axis, the first groove being configured to support the observation optical portion, and a second groove that extends along the center axis, the second groove being configured to support the first built-in material and communicate with the first groove.

In some embodiments, an ultrasound endoscope includes an insertion tube configured to be inserted into a subject, the insertion tube including a transducer that includes a plurality of piezoelectric devices that are aligned along a circumferential direction about a center axis of the insertion tube, each piezoelectric device being configured to emit ultrasound wave, an observation optical portion configured to capture a subject image, a first built-in material that is different from the observation optical portion, and a support configured to support the observation optical portion and the first built-in material, the transducer including a through hole configured to pierce through along the center axis to insert the support, and the support including a plurality of first support portions, each having a first arc shape and a second arc shape and are separated from one another on a plane perpendicular to the center axis, and a second support portion configured to integrate the first support portions, and the observation optical portion is held in the first arc shape of the plurality of first support portions, and the first built-in material is held in the second arc shape of the plurality of first support portions.

In some embodiments, provided is an insertion tube configured to be inserted into a subject. The insertion tube includes: a transducer that includes a plurality of piezoelectric devices that are aligned along a circumferential direction about a center axis of the insertion tube, each piezoelectric device being configured to emit ultrasound wave; an observation optical portion configured to capture a subject image; a first built-in material that is different from the observation optical portion; and a support configured to support the observation optical portion and the first built-in material, the transducer including a through hole configured to pierce through along the center axis to insert the support, and the support including a first groove that extends along the center axis, the first groove being configured to support the observation optical portion, and a second groove that extends along the center axis, the second groove being configured to support the first built-in material and communicate with the first groove.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes to implement the disclosure (hereinafter, embodiments) will be explained with reference to the drawings. The embodiments explained below are not intended to limit the disclosure. Furthermore, like reference signs are assigned to like parts throughout the drawings.

First Embodiment

Schematic Configuration of Endoscope System

Figure 1:
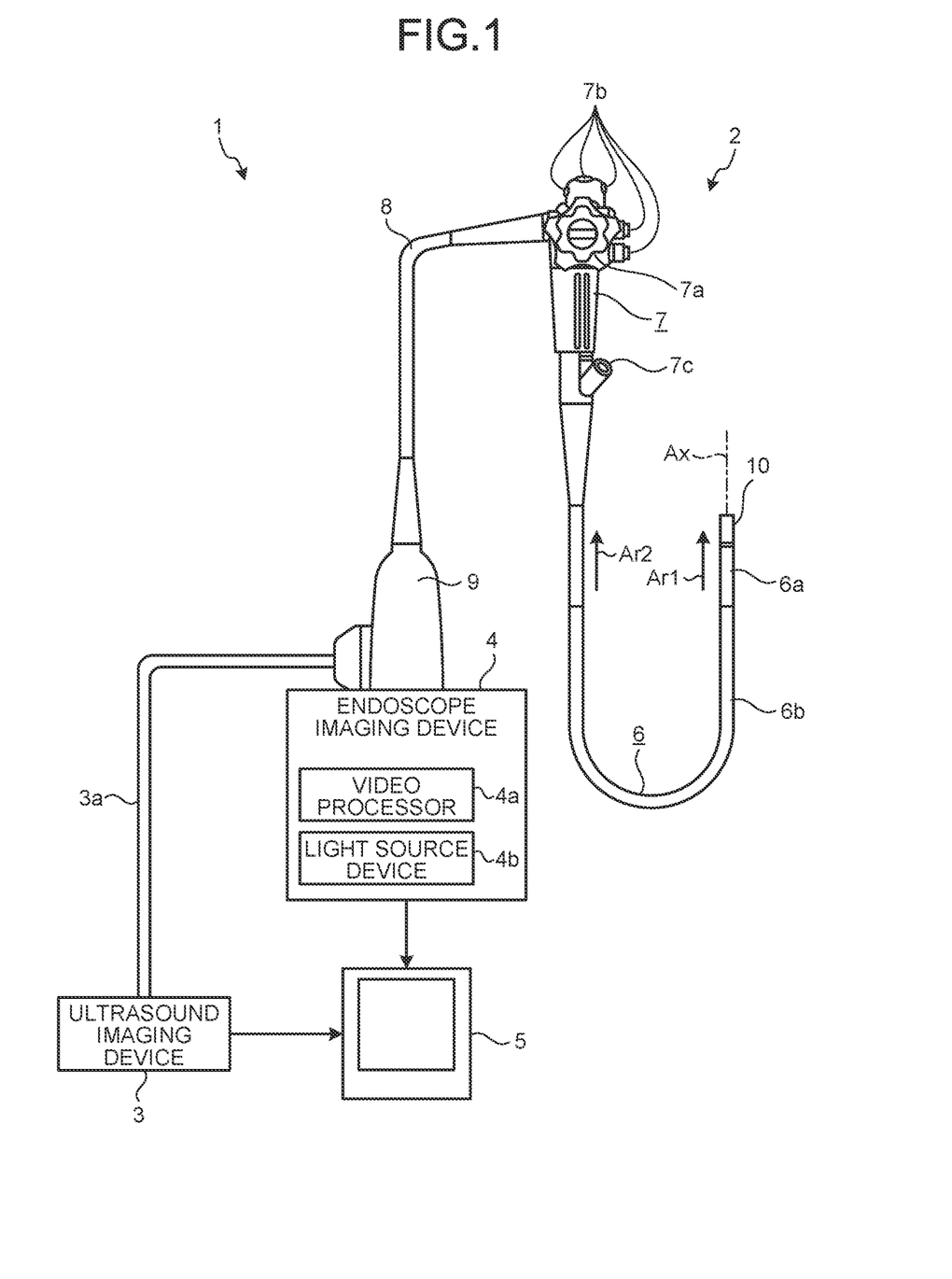
FIG. 1 is a diagram illustrating an endoscope system according to a first embodiment.

FIG. 1 is a diagram illustrating an endoscope system according to a first embodiment.

An endoscope system 1 is a system to perform ultrasound diagnosis of an inside of a subject such as human by using an ultrasound endoscope. This endoscope system 1 includes an ultrasound endoscope 2, an ultrasound imaging device 3, an endoscope imaging device 4, and a display device 5 as illustrated in FIG. 1.

The ultrasound endoscope 2 can be partially inserted into the subject. The ultrasound endoscope 2 has a function of outputting an echo signal by transmitting ultrasound pulses (acoustic pulses) toward a body wall inside the subject, and by receiving an ultrasound echo reflected by the subject, and a function of outputting an image signal by imaging an inside of the subject.

Detailed configuration of the ultrasound endoscope 2 will be described later.

The ultrasound imaging device 3 is electrically connected to the ultrasound endoscope 2 through an ultrasound cable 3a (FIG. 1). The ultrasound imaging device 3 outputs a pulse signal to the ultrasound endoscope 2, and receives an echo signal from the ultrasound endoscope 2 through the ultrasound cable 3a. Moreover, the ultrasound imaging device 3 generates an ultrasound image by subjecting the echo signal to predetermined processing.

To the endoscope imaging device 4, an endoscope connector 9 (FIG. 1) described later of the ultrasound endoscope 2 is detachably connected. As illustrated in FIG. 1, this endoscope imaging device 4 includes a video processor 4a and a light source device 4b.

The video processor 4a receives an image signal from the ultrasound endoscope 2 through the endoscope connector 9. The video processor 4a generates an endoscope image by subjecting the image signal to predetermined processing.

The light source device 4b supplies illumination light to illuminate the inside of the subject to the ultrasound endoscope 2 through the endoscope connector 9.

The display device 5 is constituted of a liquid crystal panel or an organic electroluminescence (EL) panel, and displays an ultrasound image generated by the ultrasound imaging device 3, or an endoscope image generated by the endoscope imaging device 4.

Configuration of Ultrasound Endoscope

Next, a configuration of the ultrasound endoscope 2 will be explained.

The ultrasound endoscope 2 includes an insertion tube 6, an operating unit 7, a universal cord 8, and the endoscope connector 9 as illustrated in FIG. 1.

The insertion tube 6 is a portion to be inserted into the subject. Hereinafter, for convenience of explanation, one side (a distal end side in an insertion direction into the subject) along a center axis Ax (FIG. 1) of the insertion tube 6 is denoted as a distal end side Ar1, and the other side (the operating unit 7 side) is denoted as a proximal end side Ar2.

This insertion tube 6 includes a distal end unit 10 that is arranged at a distal end, a bendable portion 6a that is connected to the proximal end side Ar2 of the distal end unit 10, and that is bendable, and a flexible tube 6b that is connected to the proximal end side Ar2 of the bendable portion 6a, and has flexibility.

A detailed configuration of the distal end unit 10 will be described later.

The operating unit 7 is a portion that is connected to the proximal end side Ar2 of the insertion tube 6, and that accepts various operations from a doctor or the like. This operating unit 7 includes a bending knob 7a to operate bending of the bendable portion 6a, and plural operating portions 7b to perform various operations as illustrated in FIG. 1. Moreover, in the operating unit 7, an instrument channel port 7c that communicates with a pipe 110 arranged in the distal end unit 10 through a tube (not illustrated) arranged inside the bendable portion 6a and the flexible tube 6b, and that is to insert a treatment tool (not illustrated), such as a puncture needle, into the tube is arranged.

The universal cord 8 extends from the operating unit 7, and is a cord in which a pair of light guides 51 (refer to FIG. 2 to FIG. 5) to transmit illumination light supplied from the light source device 4b, a transducer cable 71 (refer to FIG. 2, FIG. 3, FIG. 5) to transmit the pulse signal and the echo signal described above, a signal cable 61 (refer to FIG. 3, FIG. 5) to transmit the image signal described above, a balloon water-supply conduit (not illustrated) to let a fluid flow through, a balloon suction conduit (not illustrated), and an air and water supply conduit 81 (refer to FIG. 8) are arranged. Inside the insertion tube 6 and the operating unit 7, the pair of the light guides 51, the transducer cable 71, the signal cable 61, the balloon water-supply conduit (not illustrated), the balloon suction conduit (not illustrated), and the air and water supply conduit 81 are arranged.

The endoscope connector 9 is arranged at an end portion of the universal cord 8. The endoscope connector 9 is connected to the ultrasound cable 3a, and is connected to the video processor 4a and the light source device 4b by being inserted to the endoscope imaging device 4.

Configuration of Distal End Unit

Next, a configuration of the distal end unit 10 will be explained.

Figure 2:
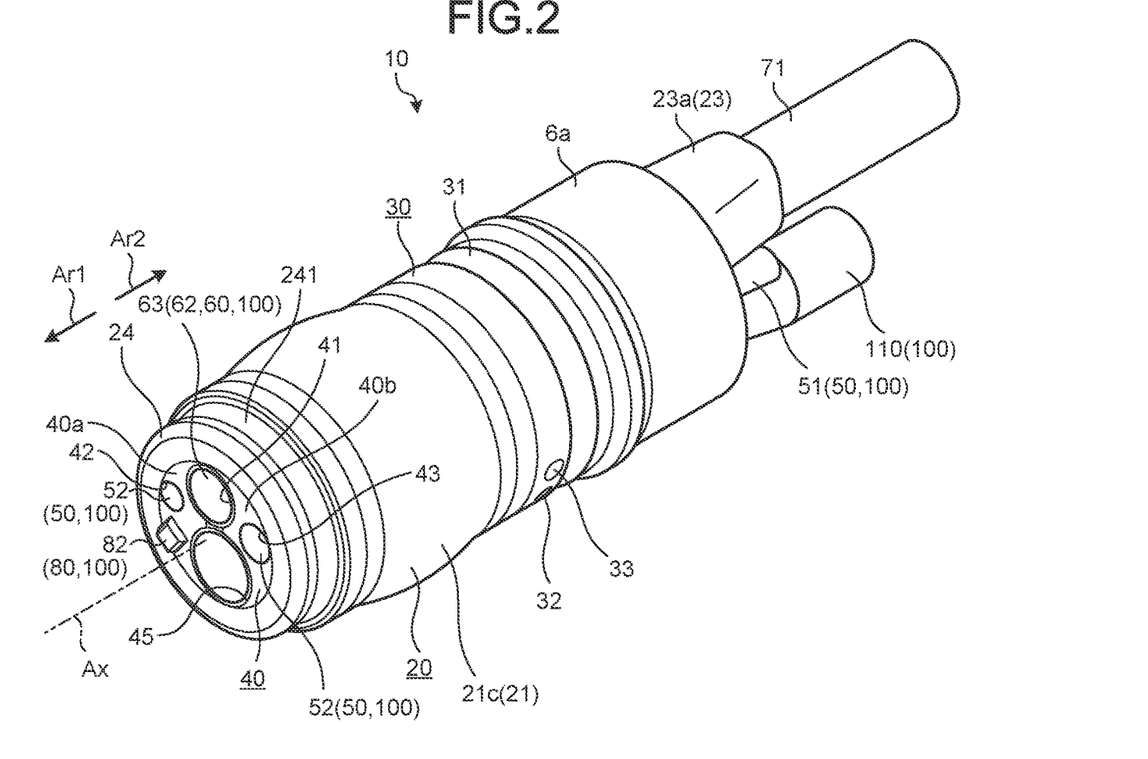
FIG. 2 is a diagram illustrating a configuration of a distal end unit.
Figure 3:
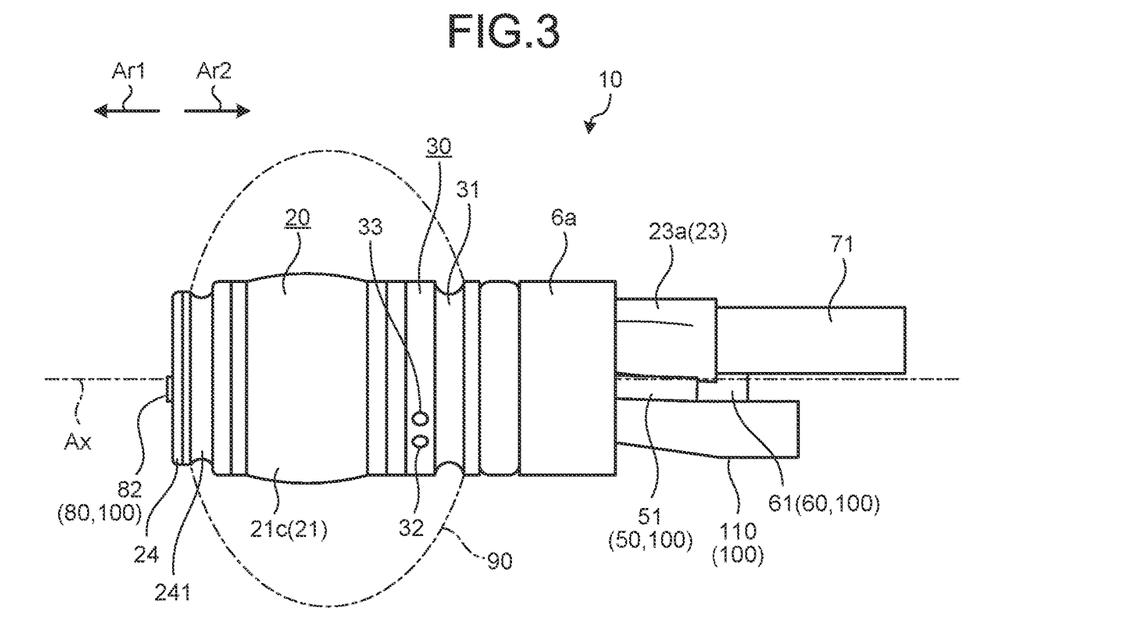
FIG. 3 is a diagram illustrating the configuration of the distal end unit.
Figure 4:
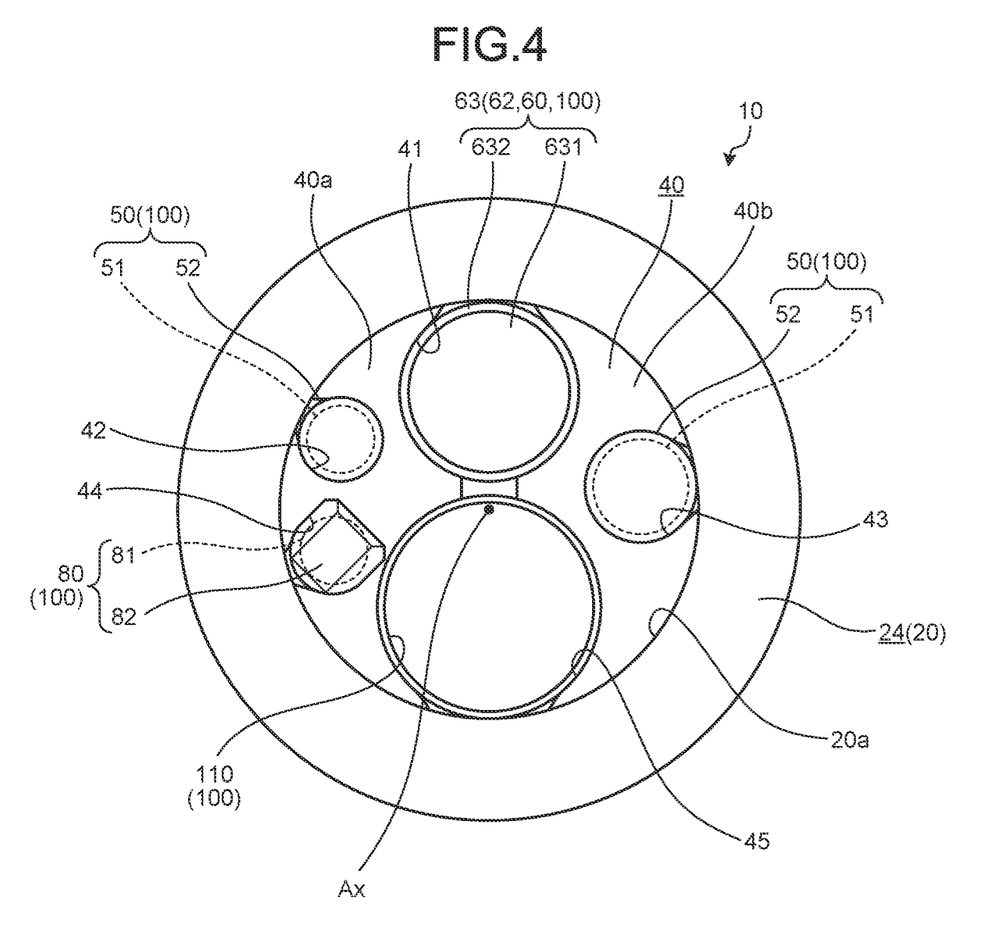
FIG. 4 is a diagram illustrating the configuration of the distal end unit.
Figure 5:
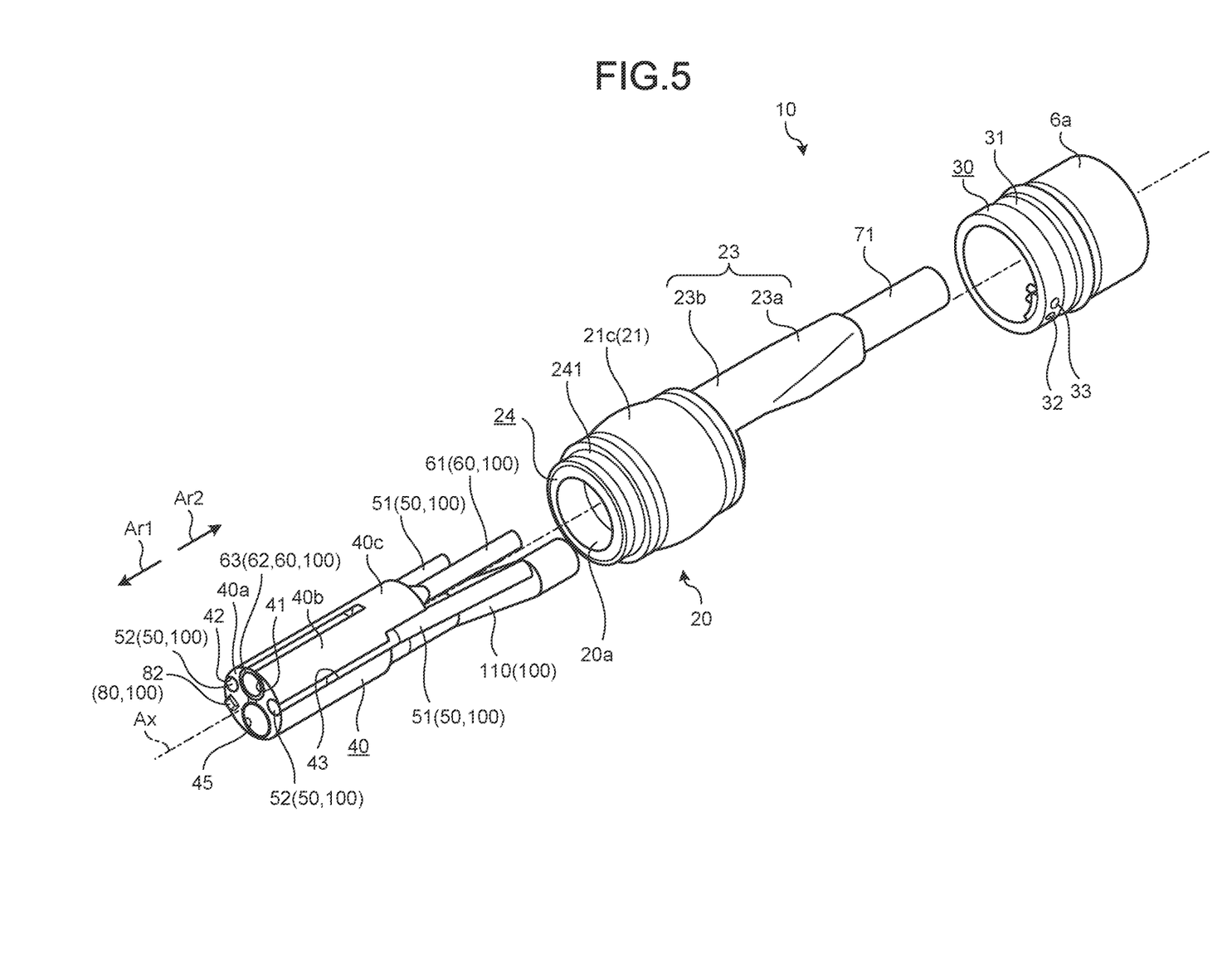
FIG. 5 is a diagram illustrating the configuration of the distal end unit.

FIG. 2 to FIG. 5 are diagrams illustrating the configuration of the distal end unit 10. Specifically, FIG. 2 is a perspective view of the distal end unit 10 viewed from the distal end side Ar1. FIG. 3 is a side view of the distal end unit 10 viewed from a direction perpendicular to the center axis Ax. FIG. 4 is a diagram illustrating a distal end of the distal end unit 10. FIG. 5 is a exploded perspective view exploding the distal end unit 10.

The distal end unit 10 includes a transducer 20, a connection portion 30 (FIG. 2, FIG. 3, FIG. 5), and a support 40 (FIG. 2, FIG. 4, FIG. 5) as illustrated in FIG. 2 to FIG. 5.

Figure 6:
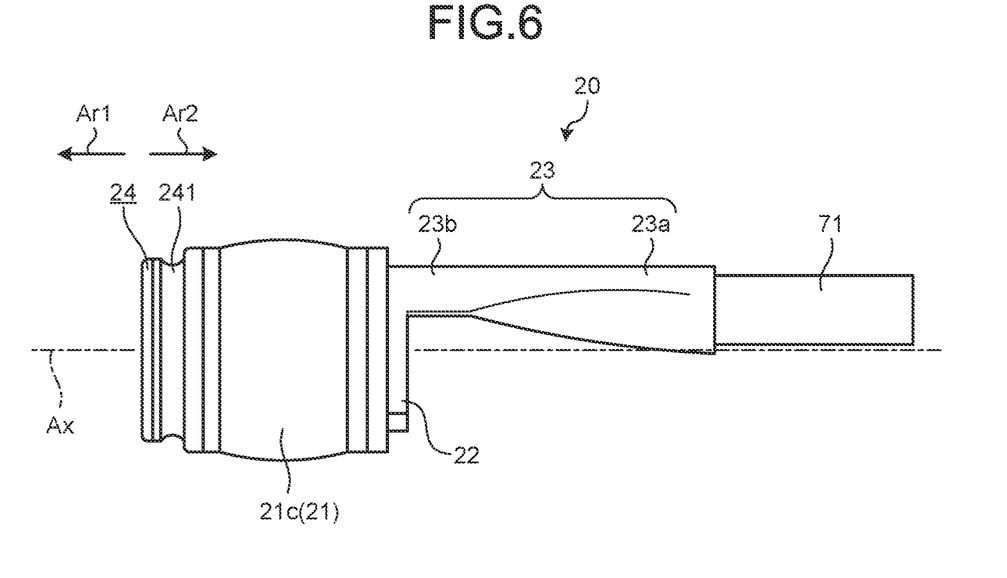
FIG. 6 is a diagram illustrating a configuration of a transducer.
Figure 7:
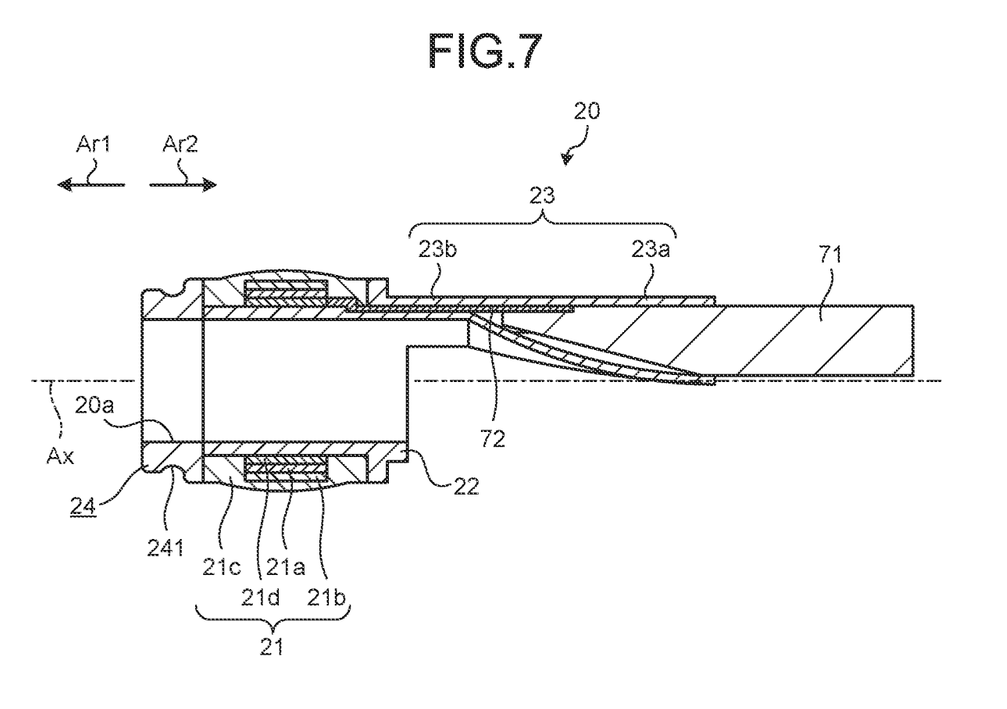
FIG. 7 is a diagram illustrating the configuration of the transducer.

FIG. 6 and FIG. 7 are diagrams illustrating a configuration of the transducer 20. Specifically, FIG. 6 is a side view of the transducer 20 viewed from a direction perpendicular to the center axis Ax. FIG. 7 is a cross-section of the transducer 20 cut on a plane including the center axis Ax.

The transducer 20 is an electronic radial scanning transducer. The transducer 20 transmits an ultrasound pulse to a direction perpendicular to the center axis Ax, and scans an ultrasound pulse in a rotating direction of 360° about the center axis Ax. This transducer 20 includes a transducer unit 21, a cylinder portion 22, a holding portion 23, and a distal end portion 24 as illustrated in FIG. 6 or FIG. 7.

The transducer unit 21 is a unit in which plural pieces of piezoelectric devices 21a, an acoustic matching layer 21b, an acoustic lens 21c, and a backing material 21d are integrated, and has a cylindrical shape coaxial to the center axis Ax as illustrated in FIG. 7.

The piezoelectric devices 21a are aligned regularly along a circumferential direction about the center axis Ax. These piezoelectric devices 21a all have the same shape, and have a rectangular parallelepiped shape extending linearly along the center axis Ax. Moreover, on an outer surface of the piezoelectric device 21a, a pair of electrodes (not illustrated) are formed. The piezoelectric device 21a converts a pulse signal input by passing through the pair of the electrodes into an ultrasound pulse, to transmit to the subject. Moreover, the piezoelectric device 21a converts an ultrasound echo reflected on the subject into an electrical echo signal.

The acoustic matching layer 21b is arranged on the piezoelectric devices 21a on an outer surface side (side being far from the center axis Ax) of the transducer unit 21, and is formed in a cylindrical shape. This acoustic matching layer 21b passes sound (ultrasound waves) efficiently between the piezoelectric device 21a and the subject and, therefore, is a portion that matches acoustic impedances between the piezoelectric device 21a and the subject.

In the first embodiment, the acoustic matching layer 21b is formed in one layer, but may be formed in two layers or more depending on characteristics of the piezoelectric devices 21a and the subject. Moreover, as for the acoustic matching layer 21b, as long as an acoustic impedance is matched with the subject, a configuration not including the acoustic matching layer 21b may be adopted.

The acoustic lens 21c is formed by using, for example, silicon resin or the like, and has a substantially cylindrical shape in which an outer peripheral surface is curved in a convex shape, and constitutes an outer surface of the transducer unit 21. Moreover, the acoustic lens 21c has a function of converging an ultrasound pulse that has been transmitted from the piezoelectric device 21a and enters through the acoustic matching layer 21b.

The acoustic lens 21c can be arranged arbitrarily, and a configuration not including the acoustic lens 21c may be adopted.

The backing material 21d is positioned on the piezoelectric devices 21a on an interior side (side close to the center axis Ax) of the transducer unit 21 as illustrated in FIG. 7, and is formed in a cylindrical shape. The backing material 21d attenuates unnecessary ultrasound vibrations caused by operations of the piezoelectric devices 21a. This backing material 21d is formed by using epoxy resin in which a filler, such as alumina or zirconia, is dispersed, or rubber in which the filler described above is dispersed.

The cylinder portion 22 is constituted of a material having an electrical insulation property, and is formed in a cylindrical shape having an outer diameter a little smaller than an inner diameter of the transducer unit 21. The transducer unit 21 is fixed to an outer circumferential surface of the cylinder portion 22 as illustrated in FIG. 7.

The holding portion 23 is constituted of a material having an electrical insulation property. In the first embodiment, the holding portion 23 is formed integrally with an end portion of the cylinder portion 22 on the proximal end side Ar2. This holding portion 23 includes a first and a second cylinder portions 23a, 23b as illustrated in FIG. 7.

The first cylinder portion 23a extends along the center axis Ax, and has a cylindrical shape having a diameter size smaller than the cylinder portion 22. The first cylinder portion 23a holds the transducer cable 71 in a state where the transducer cable 71 is inserted in the first cylinder portion 23a.

The second cylinder portion 23b has an arc shape in a cross-sectional view (cross-sectional view cut on a plane perpendicular to the center axis Ax), and is formed in a cylindrical shape extending along the center axis Ax. An end portion of the second cylinder portion 23b on the proximal end side Ar2 is connected to an end portion of the first cylinder portion 23a on the distal end side Ar1. Moreover, an end portion of the second cylinder portion 23b on the distal end side Ar1 is connected to an end portion of the cylinder portion 22 on the proximal end side Ar2. An interior of the first cylinder portion 23a communicates with space on the outer circumference side of the cylinder portion 22 through an interior of the second cylinder portion 23b.

Inside the second cylinder portion 23b explained above, a flexible substrate 72 that is electrically connected to a transducer cable 71 and the pair of electrodes (not illustrated) in the piezoelectric device 21a, and that relays the transducer cable 71 and the pair of electrodes is arranged.

The distal end portion 24 has a cylindrical shape having an inner diameter same as that of the cylinder portion 22, and is fixed to the transducer unit 21 and an end portion of the cylinder portion 22 on the distal end side Ar1 in a position coaxial with the cylinder portion 22 with an adhesive or the like as illustrated in FIG. 7.

On an outer circumferential surface of the distal end portion 24, a groove portion 241 having a ring shape that extends throughout an entire circumference in a circumferential direction about the center axis Ax as illustrated in FIG. 6 or FIG. 7, and that can catch an end portion of a balloon 90 on the distal end side Ar1 (FIG. 3), the balloon 90 being configured to fill a fluid (for example, water) in the balloon 90.

In the transducer 20 as explained above, the interior of each of the cylinder portion 22 and the distal end portion 24 pierces through along the center axis Ax, and corresponds to a through hole 20a (FIG. 7).

The connection portion 30 is formed in a cylindrical shape having an inner diameter a little larger than an outer diameter of the cylinder portion 22, and is fixed to an outer circumferential surface of the cylinder portion 22 in a state in which the holding portion 23 is inserted therein. The connection portion 30 connects the transducer 20 and the bendable portion 6a.

On an outer circumferential surface of the connection portion 30, a groove portion 31 that is formed in a ring shape extending through out an entire circumference in a circumferential direction surrounding the center axis Ax as illustrated in FIG. 2, FIG. 3, or FIG. 5, and that can catch an end portion of the balloon 90 on the proximal end side Ar2 is formed. Moreover, in the connection portion 30, a balloon water-supply hole 32 that is connected to the balloon water-supply conduit (not illustrated) described above, and a balloon suction hole 33 that is connected to the balloon suction conduit (not illustrated) described above are arranged on the distal end side Ar1 of the groove portion 31. That is, in the balloon 90, a fluid (for example, water) is filled by flowing through the balloon water-supply conduit (not illustrated) described above and the balloon water-supply hole 32. Furthermore, the fluid in the balloon 90 is sucked out by flowing through the balloon suction hole 33 and the balloon suction conduit (not illustrated) described above.

The support 40 supports a structural body 100.

Before explaining about the support 40, a configuration of the structural body 100 will be explained.

The structural body 100 includes a pair of illumination optical portions 50, an observation optical portion 60, an air and water supply portion 80, and the pipe 110 as illustrated in FIG. 2 to FIG. 5.

The pair of the illumination optical portions 50 respectively include the light guide 51 described above and an illumination lens 52 (FIG. 2, FIG. 4, FIG. 5) as illustrated in FIG. 2 to FIG. 5.

The illumination lens 52 is arranged at a position facing an emission end of the light guide 51. The illumination lens 52 illuminates illumination light emitted from the emission end of the light guide 51 to the inside of the subject.

The observation optical portion 60 includes the signal cable 61 (FIG. 3, FIG. 5) described above, and an observation optical system 62 (FIG. 2, FIG. 4, FIG. 5) as illustrated in FIG. 2 to FIG. 5.

The observation optical system 62 includes an imaging lens 63 (FIG. 2, FIG. 4, FIG. 5) configured to collect light (subject image) that has emitted to the inside of the subject from the pair of the illumination optical portions 50 and that has been reflected on the subject, and an imaging device (not illustrated) configured to capture a subject image obtained by collecting light by the imaging lens 63. An image signal obtained by imaging by the imaging device is transmitted to the endoscope imaging device 4 (the video processor 4*a*) through the signal cable 61.

In the first embodiment, the imaging lens 63 includes a lens main body 631 having a circular shape viewed from a direction along the center axis Ax, and a lens frame 632 supporting the lens main body 631 and having a cylindrical shape, as illustrated in FIG. 4.

The air and water supply portion 80 includes the air and water supply conduit 81 (FIG. 4) described above and a nozzle 82 as illustrated in FIG. 2 to FIG. 5.

The nozzle 82 is arranged at a position facing an end portion of the air and water supply conduit 81 on the distal end side Ar1. A fluid (for example, air or water) that has flowed to the distal end side Ar1 through the air and water supply conduit 81 is ejected toward an outer surface of the imaging lens 63 (the lens main body 631) by the nozzle 82. Thus, the outer surface of the imaging lens 63 (the lens main body 631) is cleaned.

The pipe 110 is a cylindrical pipe made from a material having an electrical insulation property, and is a path that allows a treatment tool (not illustrated), such as a puncture needle, inserted in the insertion tube 6 from the instrument channel port 7*c* to protrude to an outside from a distal end of the insertion tube 6.

Figure 8:
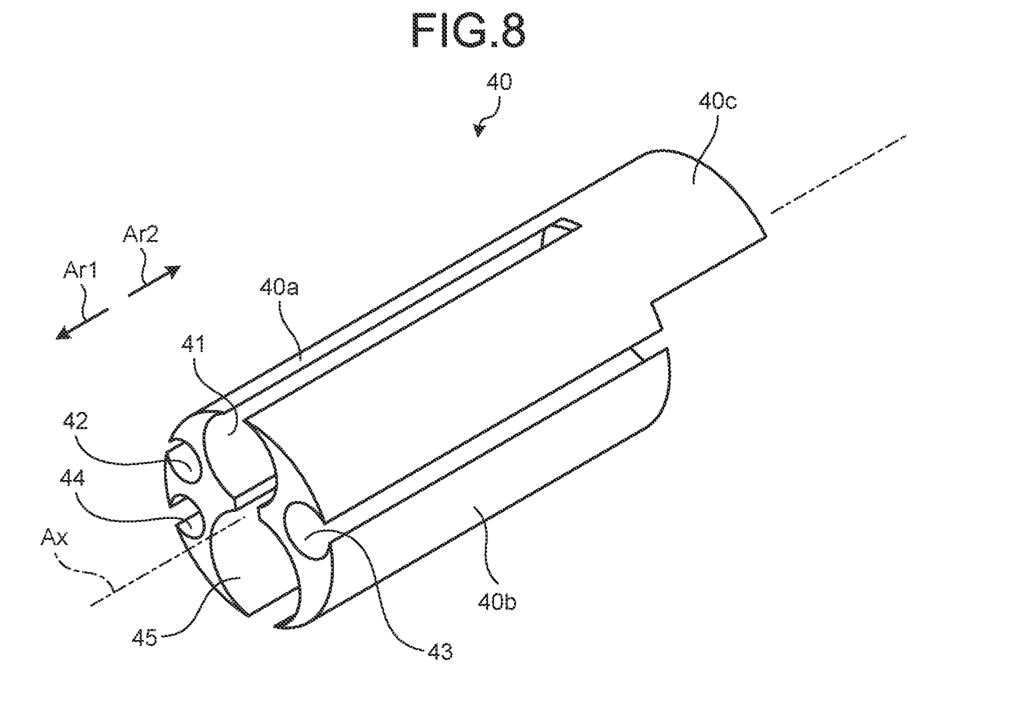
FIG. 8 is a diagram illustrating a configuration of a support.

FIG. 8 is a diagram illustrating a configuration of the support 40.

The support 40 is formed in a substantially cylindrical shape, as a whole, having an outer diameter a little smaller than an inner diameter of the through hole 20*a*.

In this support 40, as illustrated in FIG. 8, a first to a fifth concave grooves 41 to 45 extending along the center axis Ax are formed. Each of these first to the fifth concave grooves 41 to 45 corresponds to a concave groove.

The first concave groove 41 is positioned on an upper side in FIG. 8 in the support 40. This first concave groove 41 is structured as a groove by arranging a part of a circular hole at an outside of the support 40. A portion of the observation optical portion 60 on the distal end side Ar1 is supported by the support 40 in a state of being inserted in the first concave groove 41.

The second and the third concave grooves 42, 43 are respectively positioned in the support 40 on both left and right sides in FIG. 8, sandwiching a first concave groove 41. Each of these second and the third concave grooves 42, 43 is structured as a groove by arranging a part of a circular hole at an outside of the support 40, similarly to the first concave groove 41. Portions of the pair of the illumination optical portions 50 on the distal end side Ar1 are supported by the support 40 in a state of being inserted in the second and the third concave grooves 42, 43.

The fourth concave groove 44 is positioned at a lower side in FIG. 8 relative to the second concave groove 42 in the support 40. This fourth concave groove 44 is structured as a groove by arranging a part of a circular hole at an outside of the support 40, similarly to the first concave groove 41. A portion of the air and water supply portion 80 on the distal end side Ar1 is supported by the support 40 in a state of being inserted in the fourth concave groove 44.

The fifth concave groove 45 is positioned in the support 40 at a position across the center axis Ax from the first concave groove 41. This fifth concave groove 45 is structured as a groove by arranging a part of a circular hole at an outside of the support 40, similarly to the first concave groove 41. A portion of the pipe 110 on the distal end side Ar1 is supported by the support 40 in a state of being inserted in the fifth concave groove 45.

A wall portion between the first and the fifth concave grooves 41, 45 is cut off throughout an entire length of the support 40 as illustrated in FIG. 8. Therefore, the first and the fifth concave grooves 41, 45 communicate with each other. Moreover, a portion in which the second and the fourth concave grooves 42, 44 are formed and a portion in which the third concave groove 43 is formed are separated from each other on a plane perpendicular to the center axis Ax, and correspond to a first support portion 40*a* and a first support portion 40*b* (FIG. 8), respectively. Furthermore, as illustrated in FIG. 8, the two first support portions 40*a*, 40*b* are integrated by a second support portion 40*c* on the proximal end side Ar2. That is, a portion of the observation optical portion 60 on the distal end side Ar1 and a portion of the pipe 110 on the distal end side Ar1 are supported by the support 40 in a state of being sandwiched between the two first support portions 40*a* and 40*b*.

The support 40 is inserted in the through hole 20*a* in the transducer 20 in a state of supporting the structural body 100. Thus, the structural body 100 is positioned relative to the transducer 20. In this state, distal ends of the two first support portions 40*a*, 40*b* are positioned on a substantially the same plane as a distal end of the distal end portion 24. Moreover, the second support portion 40*c* is positioned outside the through hole 20*a*. A gap surrounded by the support 40 (the first to the fifth concave grooves 41 to 45), the structural body 100, and an inner surface of the through hole 20*a* is appropriately filled with adhesive or the like to ensure the watertightness.

As explained above, the ultrasound endoscope 2 according to the first embodiment is configured as a direct-view type endoscope to observe a direction along the center axis Ax.

According to the first embodiment, effects described below is produced.

Figure 9:
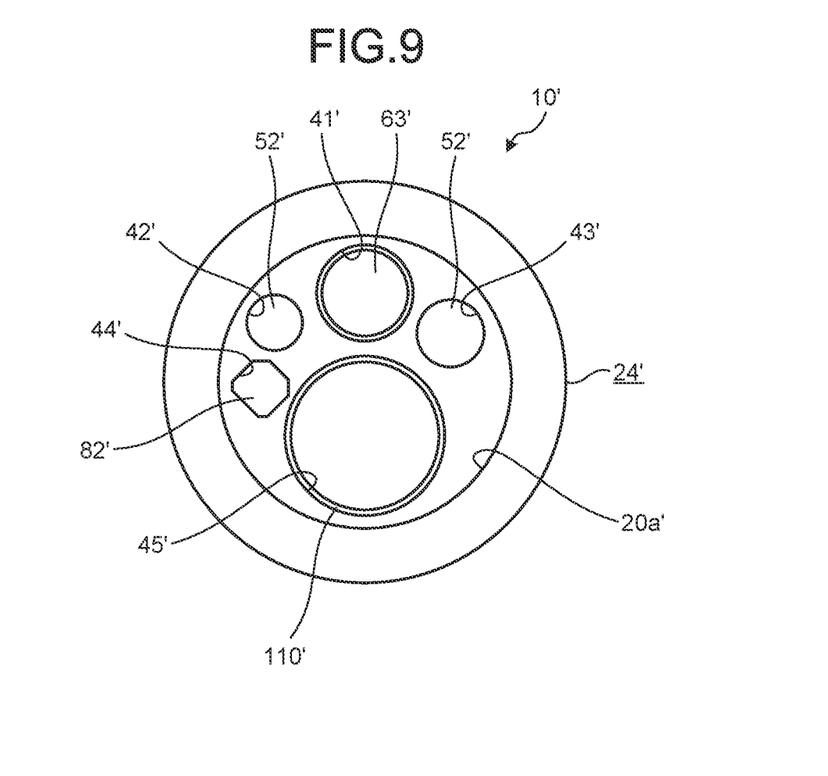
FIG. 9 is a diagram explaining an effect of the first embodiment.
Figure 10:
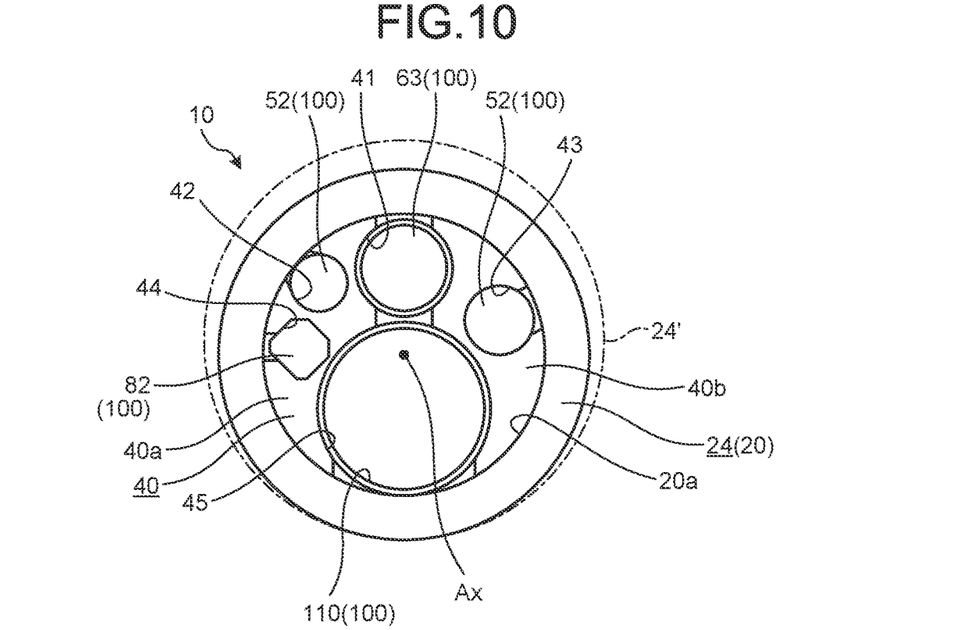
FIG. 10 is a diagram explaining an effect of the first embodiment.

FIG. 9 and FIG. 10 are diagrams explaining an effect of the first embodiment. Specifically, FIG. 9 is a diagram corresponding to FIG. 4, and is a diagram illustrating a conventional configuration in which the structural body 100 is supported by circular holes 41' to 45'. In FIG. 9, to distinguish from the distal end unit 10 according to the first embodiment, a reference symbol to which "'" is added to a reference symbol of a corresponding component is used. Moreover, in FIG. 10, a distal end portion 24' illustrated in FIG. 9 is indicated by an alternate long and short dash line.

In the conventional configuration, as illustrated in FIG. 9, a part to support the structural body 100 in a support 40' is constituted of the circular holes 41' to 45'. That is, the circular holes 41' to 45' are arranged with a portion between an outer circumferential surface of the support 40' and an inner surface of the circular holes 41' to 45', the portion having a thickness of a predetermined size. Therefore, depending on the size of the thickness of the portion, the support 40' cannot be made thin.

On the other hand, in the ultrasound endoscope 2 according to the first embodiment, as illustrated in FIG. 10, the first to the fifth concave grooves 41 to 45 extending along the center axis Ax are arranged in the support 40. The structural body 100 is supported by the support 40 in a state of being inserted in the first to the fifth concave grooves 41 to 45. Moreover, the support 40 is inserted to the through hole 20a while supporting the structural body 100.

Since the part (the first to the fifth concave grooves 41 to 45) to support the structural body 100 in the support 40 is structured as grooves, a portion between the outer surface of the support 40 and the supporting part (the first to the fifth concave grooves 41 to 45) is eliminated, the portion having a thickness of a predetermined size. Accordingly, it is possible to make the diameter of the support 40 thin and further make the diameter of the insertion tube 6 thin.

Moreover, in the ultrasound endoscope 2 according to the first embodiment, the first and the fifth concave grooves 41, 45 communicate with each other.

Therefore, the wall portion between the first and the fifth concave grooves 41 and 45 can also be eliminated, the wall portion having a thickness of a predetermined size, and thus it is possible to further make the diameter of the insertion tube 6 thin.

Furthermore, in the ultrasound endoscope 2 according to the first embodiment, the pipe 110 is inserted in the fifth concave groove 45.

Since the pipe 110 is arranged in a position corresponding to a treatment tool channel in which a treatment tool, such as a puncture needle, is inserted, even if the fifth concave groove 45 is used instead of the circular hole 45', the watertightness can be sufficiently obtained.

Second Embodiment

Next, a second embodiment will be explained.

In the following explanation, identical reference signs are assigned to components same as those in the first embodiment, and detailed explanation thereof will be omitted or simplified.

Figure 11:
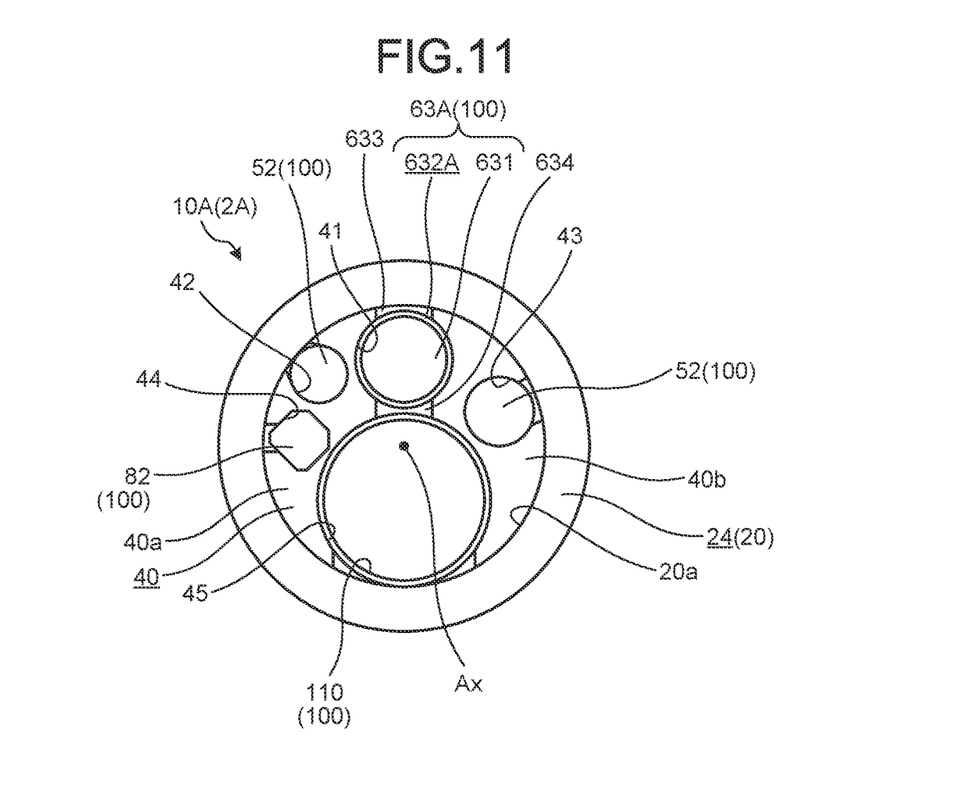
FIG. 11 is a diagram illustrating a configuration of a distal end unit according to a second embodiment.
Figure 12:
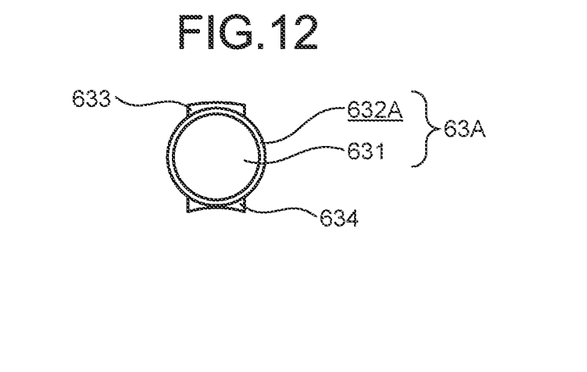
FIG. 12 is a diagram illustrating a configuration of an imaging lens.

FIG. 11 is a diagram illustrating a configuration of a distal end unit 10A according to the second embodiment. Specifically, FIG. 11 is a diagram illustrating a distal end of the distal end unit 10A. FIG. 12 is a diagram illustrating a configuration of an imaging lens 63A. Specifically, FIG. 12 is a diagram of the imaging lens 63A viewed from a direction along the center axis Ax.

In an ultrasound endoscope 2A according to the second embodiment, as illustrated in FIG. 11 or FIG. 12, a lens frame 632A in a different shape from the lens frame 632 is adopted to the ultrasound endoscope 2 explained in the first embodiment described above.

Specifically, the lens frame 632A is obtained by adding a first protruding portion 633 and a second protruding portion 634 to the lens frame 632 explained in the first embodiment described above.

The first protruding portion 633 is a portion protruding toward an inner surface of the through hole 20a as illustrated in FIG. 11 or FIG. 12. A tip of the first protruding portion 633 has a shape fitting the inner surface of the through hole 20a. That is, an outer surface of the imaging lens 63A (the lens frame 632A) facing the inner surface of the through hole 20a has a shape fitting the inner surface of the through hole 20a.

The second protruding portion 634 is a portion that protrudes toward the pipe 110 as illustrated in FIG. 11 or FIG. 12. A tip of the second protruding portion 634 has a shape fitting an outer surface of the pipe 110. That is, an outer surface of the imaging lens 63A (the lens frame 632A) facing the pipe 110 has a shape fitting the outer surface of the pipe 110.

According to the second embodiment explained above, following effects in addition to effects similar to those of the first embodiment described above are produced In the ultrasound endoscope 2A according to the second embodiment, the outer surface of the imaging lens 63A facing the inner surface of the through hole 20a has a shape fitting the inner surface of the through hole 20a. Moreover, the outer surface of the imaging lens 63A facing the pipe 110 has a shape fitting the outer surface of the pipe 110.

That is, by making the outer surface of the imaging lens 63A into the form described above, an amount of adhesive to be filled in a gap surrounded by the imaging lens 63A, the first concave groove 41, the inner surface of the through hole 20a, and the pipe 110 can be reduced. Therefore, tolerance to a damage by a chemical solution can be improved.

In the second embodiment described above, the outer surface of the imaging lens 63A is formed in the shape described above, but it is not limited thereto. As long as it is the structural body 100 supported by the support 40, other outer surfaces of the structural body 100 facing the inner surface of the through hole 20a may be formed in a shape fitting the inner surface of the through hole 20a. Moreover, in the first embodiment described above, an outer surface of the pipe 110 facing the imaging lens 63 may be formed in a shape fitting the outer surface of the imaging lens 63.

Third Embodiment

Next, a third embodiment will be explained.

In the following explanation, identical reference signs are assigned to components similar to those of the first embodiment described above, and detailed explanation will be omitted or simplified.

Figure 13:
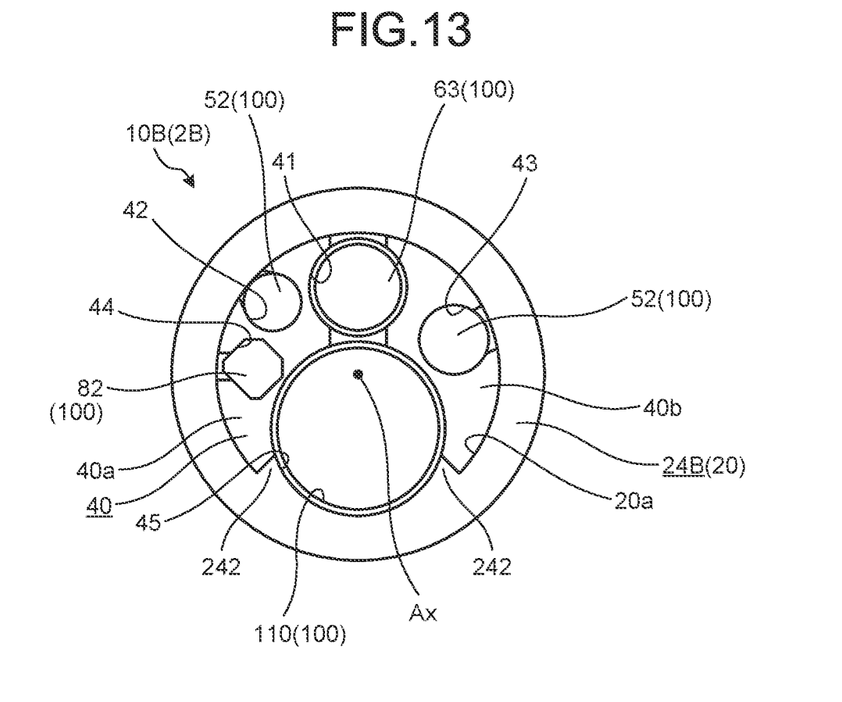
FIG. 13 is a diagram illustrating a configuration of a distal end unit according to a third embodiment.
Figure 14:
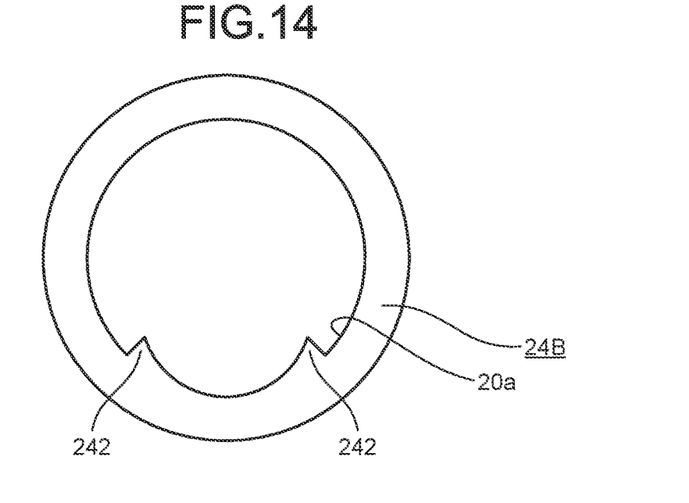
FIG. 14 is a diagram illustrating a configuration of a distal end portion.

FIG. 13 is a diagram illustrating a configuration of a distal end unit 10B according to the third embodiment. Specifically, FIG. 13 is a diagram illustrating a distal end of the distal end unit 10B. FIG. 14 is a diagram illustrating a configuration of a distal end portion 24B. Specifically, FIG. 13 is a diagram illustrating the distal end portion 24B viewed from a direction along the center axis Ax.

In an ultrasound endoscope 2B according to the third embodiment, as illustrated in FIG. 13 or FIG. 14, the distal end portion 24B having a shape different from the distal end portion 24 is adopted to the ultrasound endoscope 2 explained in the first embodiment described above.

Specifically, in the distal end portion 24B, a pair of protruding portions 242 that protrude from the inner surface of the through hole 20a toward the pipe 110 are arranged as illustrated in FIG. 13 or FIG. 14. Respective tips of these pair of the protruding portions 242 have a shape fitting the outer surface of the pipe 110. That is, the inner surface of the through hole 20a facing the pipe 110 has a shape fitting the outer surface of the pipe 110.

The pair of the protruding portions 242 may be arranged only in the distal end portion 24B, or may be arranged both in the distal end portion 24B and in the cylinder portion 22, and may be formed to extend throughout the entire length of the through hole 20a.

According to the third embodiment explained above, following effects other than effects similar to those of the first embodiment described above are produced.

In the ultrasound endoscope 2B according to the third embodiment, the inner surface of the through hole 20a facing the pipe 110 is formed in a shape fitting the outer surface of the pipe 110.

That is, by forming the inner surface of the through hole 20a in a shape described above, an amount of adhesive to be filled in a gap surrounded by the pipe 110, the fifth concave groove 45, and the inner surface of the through hole 20a can be reduced. Therefore, tolerance to a damage by a chemical solution can be improved.

In the third embodiment, the inner surface of the through hole 20a facing the pipe 110 is formed in the shape described above, but it is not limited thereto. As long as it is the structural body 100 supported by the support 40, other inner surface of the through hole 20a facing the structural body 100 may be formed in a shape fitting the outer surface of the structural body 100.

Fourth Embodiment

Next, a fourth embodiment will be explained.

In the following explanation, identical reference signs are assigned to components similar to those of the first embodiment described above, and detailed explanation will be omitted or simplified.

Figure 15:
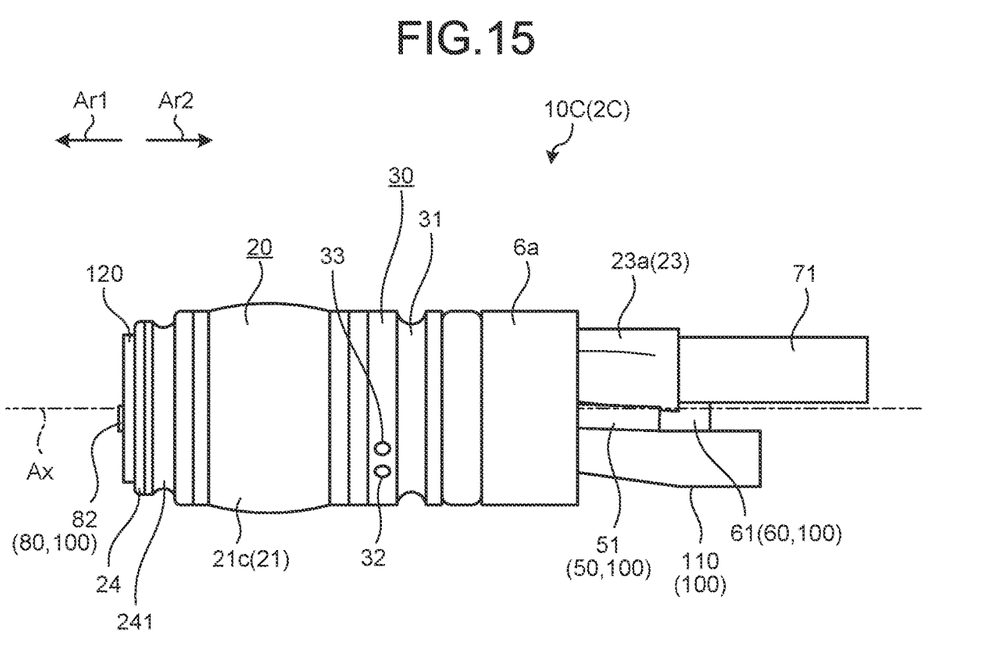
FIG. 15 is a diagram illustrating a configuration of a distal end unit according to a fourth embodiment.
Figure 16:
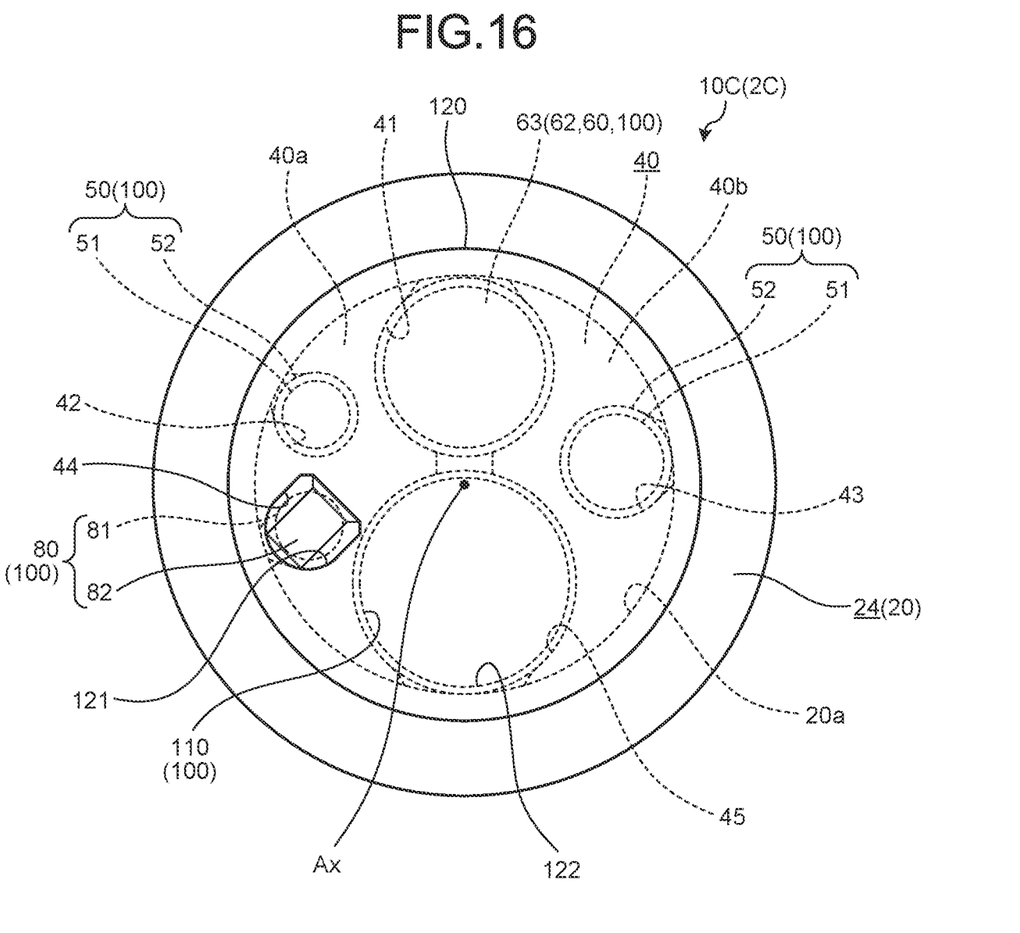
FIG. 16 is a diagram illustrating the configuration of the distal end unit according to the fourth embodiment.

FIG. 15 and FIG. 16 are diagrams illustrating a configuration of a distal end unit 10C according to the fourth embodiment. Specifically, FIG. 15 is a side view of the distal end unit 10C viewed from a direction perpendicular to the center axis Ax. FIG. 16 is a diagram illustrating a distal end of the distal end unit 10C.

In an ultrasound endoscope 2C according to the fourth embodiment, as illustrated in FIG. 15 or FIG. 16, a cover 120 is added to the ultrasound endoscope 2 explained in the first embodiment described above.

The cover 120 is a flat plate made from a material having a translucency, and covers a distal end of the support 40 by being attached to the distal end of the distal end portion 24.

In the cover 120, a hole 121 and a hole 122 that pierce through to a front and a rear surfaces are formed at a position corresponding to the air and water supply portion 80, and at a position corresponding to the pipe 110, respectively, as illustrated in FIG. 16. That is, a fluid passing through the air and water supply portion 80 is ejected from the hole 121 (the nozzle 82) toward the position facing the imaging lens 63 in the cover 120. Moreover, a treatment tool (not illustrated), such as a puncture needle, passing through the pipe 110 protrudes out to the outside from the hole 122.

According to the fourth embodiment explained above, following effects other than effects similar to those of the first embodiment is produced.

In the ultrasound endoscope 2C according to the fourth embodiment, the cover 120 to cover the distal end of the support 40 is arranged.

Therefore, an amount of adhesive exposing to the outer surface (adhesive to be filled in a gap surrounded by the support 40 (the first to the fifth concave grooves 41 to 45), the structural body 100, and the inner surface of the through hole 20a) can be reduced, and tolerance to a damage by a chemical solution can be improved.

In the fourth embodiment described above, the holes 121, 122 are formed only at positions corresponding to the nozzle 82 and the pipe 110 in the cover 120, but it is not limited thereto, and the holes 121, 122 may be formed also at a position corresponding to the imaging lens 63 or the illumination lens 52. That is, the imaging lens 63 and the illumination lens 52 may be covered or not covered with the cover 120.

Other Embodiments

The embodiments to implement the disclosure have so far been explained, but the disclosure is not to be limited only to the first to the fourth embodiments described above.

In the first to the fourth embodiments described above, the ultrasound endoscope 2 (2A to 2C) may be mounted on an endoscope system to observe an inside of a subject, such as a mechanical structure, in an industrial field, not limited to a medical field.

According to the ultrasound endoscope according to the disclosure, it is possible to make the diameter of an insertion tube thin.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope comprising:
an insertion tube configured to be inserted into a subject, the insertion tube comprising:
a transducer comprising a plurality of piezoelectric devices aligned along a circumferential direction about a center axis of the insertion tube, each piezoelectric device being configured to emit an ultrasound wave, the transducer including a through hole configured to pierce through along the center axis,
an observation optical portion configured to capture a subject image,
a first built-in material different from the observation optical portion, and
a support disposed in the through hole, the support being configured to hold the observation optical portion and the first built-in material,
the support comprising:
a first groove extending in a center axis direction, the first groove being configured to hold the observation optical portion,
a second groove extending in the center axis direction, the second groove being configured to hold the first built-in material, and
a connecting groove extending in the central axis direction in a central portion of the support to connect the first groove to the second groove at the central portion.

2. The ultrasound endoscope according to claim 1, wherein
the first built-in material is an illumination optical portion configured to illuminate illumination light to the subject, and
the observation optical portion and the illumination optical portion are inserted in the first groove and the second groove, respectively, and are supported by the support.

3. The ultrasound endoscope according to claim 1, wherein
the first built-in material is an air and water supply portion to let a fluid flow through, and
the observation optical portion and the air and water supply portion are inserted in the first groove and the second groove, respectively, and are supported by the support.

4. The ultrasound endoscope according to claim 1, wherein
the first built-in material is a pipe in which a treatment tool is inserted, and
the observation optical portion and the pipe are inserted in the first groove and the second groove, respectively, and are supported by the support.

5. The ultrasound endoscope according to claim 4, wherein
the pipe is made from a material having an electrical insulation property.

6. The ultrasound endoscope according to claim 1, wherein at least two out of an outer surface of the observation optical portion, an outer surface of the first built-in material, and an inner surface of the through hole each have a shape fitting each other.

7. The ultrasound endoscope according to claim 6, wherein
the at least two out of the outer surface of the observation optical portion, the outer surface of the first built-in material, and the inner surface of the through hole each have a curved surface of a curvature equal to each other.

8. The ultrasound endoscope according to claim 6, wherein
at least one out of the outer surface of the observation optical portion, the outer surface of the first built-in material, and the inner surface of the through hole has a protruding portion, and
the protruding portion has the fitting shape.

9. The ultrasound endoscope according to claim 1, further comprising a cover that covers a distal end of the support.

10. An ultrasound endoscope comprising:
an insertion tube configured to be inserted into a subject, the insertion tube comprising:
a transducer comprising a plurality of piezoelectric devices aligned along a circumferential direction about a center axis of the insertion tube, each piezoelectric device being configured to emit an ultrasound wave, the transducer including a through hole configured to pierce through along the center axis,
a first built-in material that is at least one of an observation optical portion configured to capture a subject image, and a pipe in which a treatment tool is inserted, and
a support disposed in the through hole, the support being configured to hold the first built-in material,
the support comprising:
a plurality of first support portions separated from one another on a plane perpendicular to the center axis at a first longitudinal portion of the support, and
a second support portion configured to connect the plurality of first support portions at a second longitudinal portion of the support different from the first longitudinal portion of the support,
wherein each of the plurality of first support portions has a first surface, and
the first built-in material is held between adjacent first surfaces of the plurality of first support portions.

11. An insertion tube configured to be inserted into a subject, the insertion tube comprising:
a transducer comprising a plurality of piezoelectric devices aligned along a circumferential direction about a center axis of the insertion tube, each piezoelectric device being configured to emit an ultrasound wave, the transducer including a through hole configured to pierce through along the center axis;
an observation optical portion configured to capture a subject image;
a first built-in material different from the observation optical portion; and
a support disposed in the through hole, the support being configured to hold the observation optical portion and the first built-in material,
the support comprising:
a first groove extending in a center axis direction, the first groove being configured to hold the observation optical portion,
a second groove extending in the center axis direction, the second groove being configured to hold the first built-in material, and
a connecting groove extending in the central axis direction in a central portion of the support to connect the first groove to the second groove at the central portion.

12. The ultrasound endoscope according to claim 10, wherein the second support portion is positioned outside the through hole.

13. The ultrasound endoscope according to claim 10, wherein
the first built-in material is the observation optical portion,
each of the plurality of first support portions has a second surface, and
further comprising at least one of the illumination optical portion, the air and water supply portion, and the pipe held between second surfaces of the plurality of first support portions.

14. The ultrasound endoscope according to claim 10, wherein the first longitudinal portion of the support is a distal portion of the support and the second longitudinal portion of the support is a proximal portion of the support.

15. The ultrasound endoscope according to claim 1, wherein in a cross section perpendicular to the center axis, a sum of a diameter of the first groove and a diameter of the second groove is smaller than an inner diameter of the through hole.

16. The ultrasound endoscope according to claim 15, wherein in the cross section perpendicular to the center axis, each of the first groove and the second groove has a circular shape.

17. The ultrasound endoscope according to claim 1, wherein the support further comprising:
a plurality of first support portions separated from one another on a plane perpendicular to the center axis at a first longitudinal portion of the support, and
a second support portion configured to connect the plurality of first support portions at a second longitudinal portion of the support different from the first longitudinal portion of the support.

18. The ultrasound endoscope according to claim 17, wherein the first longitudinal portion of the support is a distal portion of the support and the second longitudinal portion of the support is a proximal portion of the support.

19. The insertion tube according to claim 11, wherein the support further comprising:
a plurality of first support portions separated from one another on a plane perpendicular to the center axis at a first longitudinal portion of the support, and
a second support portion configured to connect the plurality of first support portions at a second longitudinal portion of the support different from the first longitudinal portion of the support.

20. The insertion tube according to claim 19, wherein the first longitudinal portion of the support is a distal portion of the support and the second longitudinal portion of the support is a proximal portion of the support.

21. The ultrasound endoscope according to claim 1, wherein the connecting groove comprising first and second side surfaces spaced apart from each other at a first width in a direction orthogonal to the center axis direction, the first width being wider than a width of each of the first groove and the second groove in the direction orthogonal to the center axis direction.

22. The insertion tube according to claim 11, wherein the connecting groove comprising first and second side surfaces spaced apart from each other at a first width in a direction orthogonal to the center axis direction, the first width being wider than a width of each of the first groove and the second groove in the direction orthogonal to the center axis direction.

* * * * *